United States Patent [19]
Maxwell

[11] Patent Number: 6,024,715
[45] Date of Patent: Feb. 15, 2000

[54] WRIST BRACE

[76] Inventor: Richard Maxwell, 301 N. Broad St., Grove City, Pa. 16127

[21] Appl. No.: 09/114,312

[22] Filed: Jul. 13, 1998

[51] Int. Cl.[7] ........................................ A61F 13/00
[52] U.S. Cl. ................................... 602/64; 602/21
[58] Field of Search ........................... 602/5, 20, 21, 602/60–64; 128/878, 879; 2/16, 18, 20, 162, 161.1, 910

[56] References Cited

U.S. PATENT DOCUMENTS

| | | | |
|---|---|---|---|
| 3,327,703 | 6/1967 | Gamm . | |
| 4,441,490 | 4/1984 | Nirschl . | |
| 4,869,267 | 9/1989 | Grim et al. | 602/27 |
| 4,884,297 | 12/1989 | Triche | 2/910 X |
| 5,267,943 | 12/1993 | Dancyger | 602/5 |
| 5,513,657 | 5/1996 | Nelson | 128/879 |
| 5,526,531 | 6/1996 | Olson et al. . | |
| 5,538,501 | 7/1996 | Caswell | 602/21 X |
| 5,769,804 | 6/1998 | Harris et al. | 602/20 X |

Primary Examiner—Richard J. Apley
Assistant Examiner—Denise Pothier
Attorney, Agent, or Firm—Harpman & Harpman

[57] ABSTRACT

A fabric brace used in supporting a human wrist having a main enclosure body with a slip-on elastic sleeve formed thereon by a wide fabric strip. An adjustable thumb engagement strap and restraint engagement strap together tighten the brace about the human wrist and hand. Stiffening insert bars are positioned in pockets in the enclosure body. The wrist engagement strap provides an enlarged area of contact with the enclosure body so as to adjustably position and effectively hold the brace about the user's wrist.

10 Claims, 5 Drawing Sheets ical Field

This device relates to improvements to wrist braces used to support the wrist for therapeutic reasons. These types of braces are used for rehabilitation and preventing injuries to the wrist common in repetitive motion situations by supporting and bracing the muscles, tendons, fascia, nerves and bones of the wrist by applying a supportive uniform pressure thereon.

2. Description of Prior Art

Prior art devices of this type have relied on a variety of different designs and constructions to support wrist during repetitive actions such as typing, cumulative trauma or sport related repetitive motions which impart injury, etc. Accordingly, a number of prior art devices have been developed in recent years that are made of reinforced synthetic fabric material, such as nylon that use multiple securing straps that are typically secured to oppositely disposed portions of the braces by velcro type hook and loop fasteners, see for example U.S. Pat. Nos. 5,526,531, 4,441,490 and 3,327,703.

In U.S. Pat. No. 5,526,531, a wrist guard is disclosed having a sleeve configuration with a plurality of closure straps that extend through respective registering loops.

U.S. Pat. No. 4,441,490 is directed to a fabric wrist brace having a number of adjustment and securing straps extending therefrom that extend around the brace on the wrist and about the portion of the user's hand forming a criss-cross overlapping configuration. A reinforcing stay adds additional rigidity and support to the back side of the brace and hand extending portion.

U.S. Pat. No. 3,327,703 is directed towards a wrist brace which is configured in a sleeve-like shape designed to maintain the wrist in a healing position while at the same time preventing sufficient voluntary flexing movement to prevent atrophy or weakening of the muscles due to inactivity which would result if the wearers hand was completely immobilized. The sleeve-like configuration has a reinforcing element which is inserted therein to provide longitudinal contoured rigidity support to the structure.

A number of wrist braces as evident by design patents have also been devised in prior art, for example, U.S. Design Pat. No. D259,955 which shows a elongated sleeve configuration with oppositely disposed openings so as to be used for either right or left handed with a contoured strap that extends thereabout just below the thumb portion.

Other prior art wrist brace configurations typically include a fabric body member, multiple support and securing straps and rigid reinforcing inserts. An example of such would be a wrist brace produced by Smith & Nephew Rolyan where a fabric brace is formed with a sleeve-like configuration having a fixed opening for the user's thumb and a plurality of adjustable straps extending transversely across the resilient portion of the sleeve.

SUMMARY OF THE INVENTION

A wrist brace having a reinforced main flexible fabric body with an adjustable thumb engagement strap extending therefrom. An elastic band extending inwardly from the perimeter edge of the body member to its oppositely disposed edge to form a partial sleeve therebetween for ease of use. A resilient adjustable fastening strap extends from the edge of the main body member and is registerable through a fixed D-ring fitting spaced inwardly on the opposing edge of the main body member so as to be returned upon itself and re-attached adjacent its point of origin. Velcro fastening strips are secured to the outer surface of the body member and are strategically placed so as to selectively be engaged by the perspective thumb engagement strap and resilient adjustable fastening strap.

DESCRIPTION OF THE PREFERRED EMBODIMENT

Figure 1:
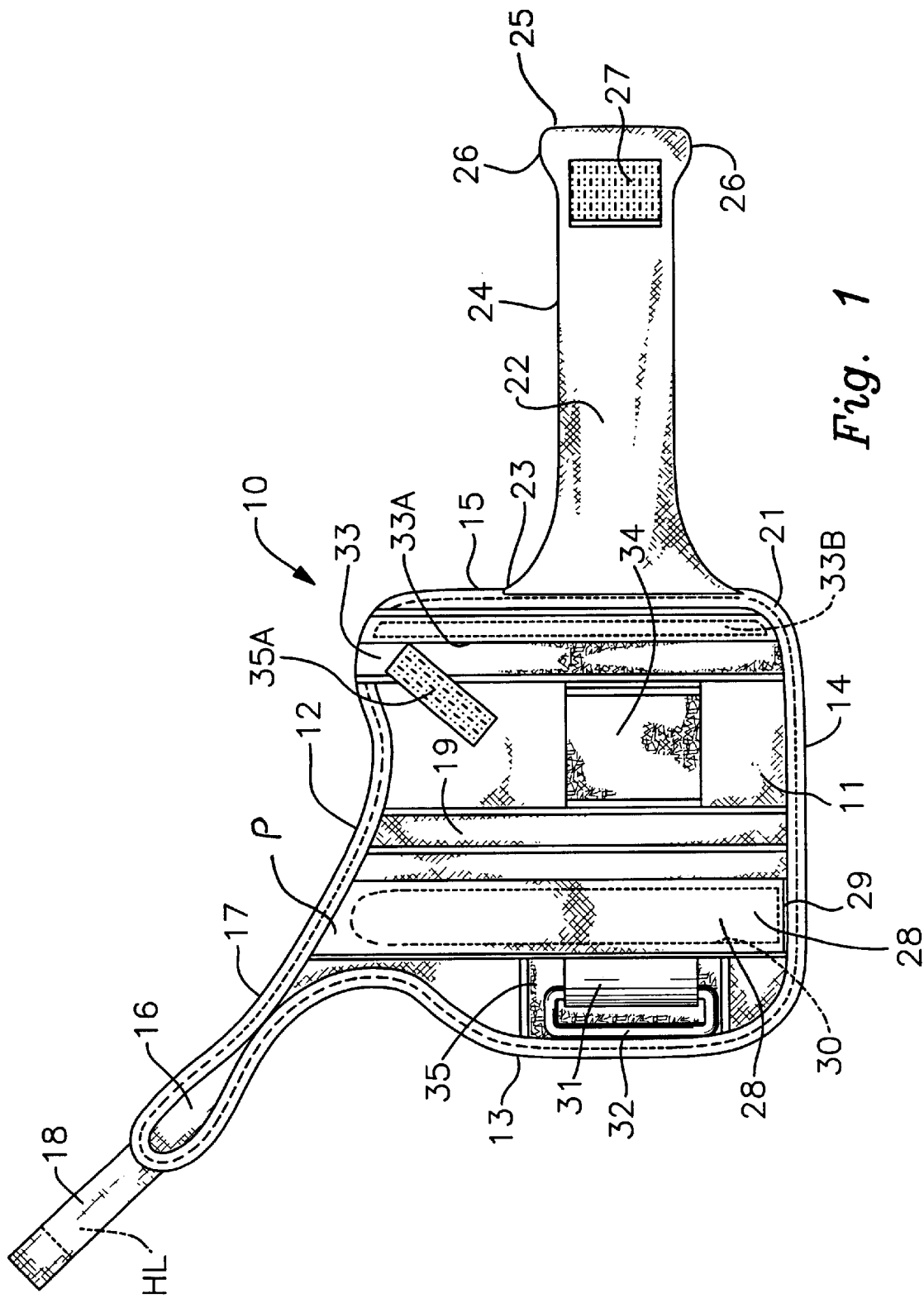
FIG. 1 is a top plan view of the wrist brace of the present invention.

Referring to FIG. 1 of the drawings, a wrist brace 10 of the invention can be seen comprising, an elongated main pad 11 with a contoured upper edge 12 and side edge 13 with oppositely disposed longitudinally straight bottom edge 14 and side edge 15.

A thumb strap 16 extends from the junction of the contoured edges 12 and 13 having an area of reduced transverse dimension at 17 terminating at a fastening strap 18 extending therefrom with a velcro type hook and loop material HL thereon. A reinforcing strip 19 extends from the upper edge 12 across the pad 11 to the oppositely disposed bottom edge 14 defining a fold point for the main pad 11. Correspondingly, the pad 11 and integral thumb strap 16 are preferably made from synthetic foam laminate material having a foam core and outside exterior non-elastic synthetic surfaces with a binder strip 21 stitched around the entire perimeter edge thereof.

A main securing strap 22 extends outwardly from opposite side edge 15 in spaced relation from the bottom edge 14 and is of an elastic foam material that has a determined rebound characteristics thereto. The strap 22 tapers inwardly from its main mounting area 23 on the pad 11 to a uniform width at 24 with its distal end 25 having enlarged transverse tab-like extensions at 26 as will be well understood by those skilled in the art. An area of hook material 27 is secured to the strap 22 inwardly of its distal end so as to secure same in operation to the main pad 11 as will be hereinafter described. An reinforced fabric strip 28 is secured in parallel spaced relation to said hereinbefore described strip 19 about its three respective perimeter edges as best seen in FIG. 1 of the drawings so as to define an elongated insert pocket with an opening at 29 adjacent the bottom edge 14.

Figure 4:
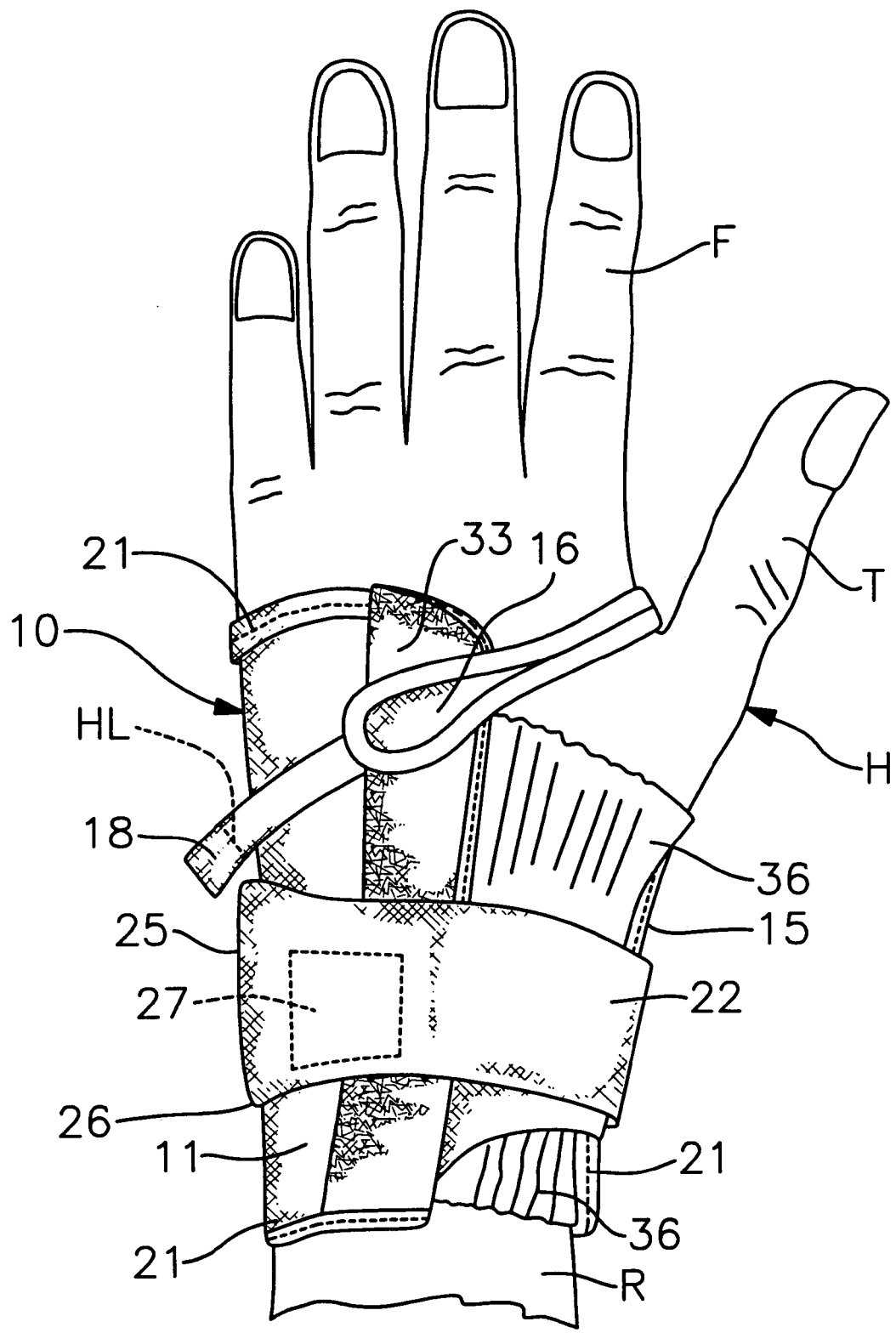
FIG. 4 is top plan view of the wrist brace of the invention secured to the wrist and hand of a user.
Figures 5, 6:
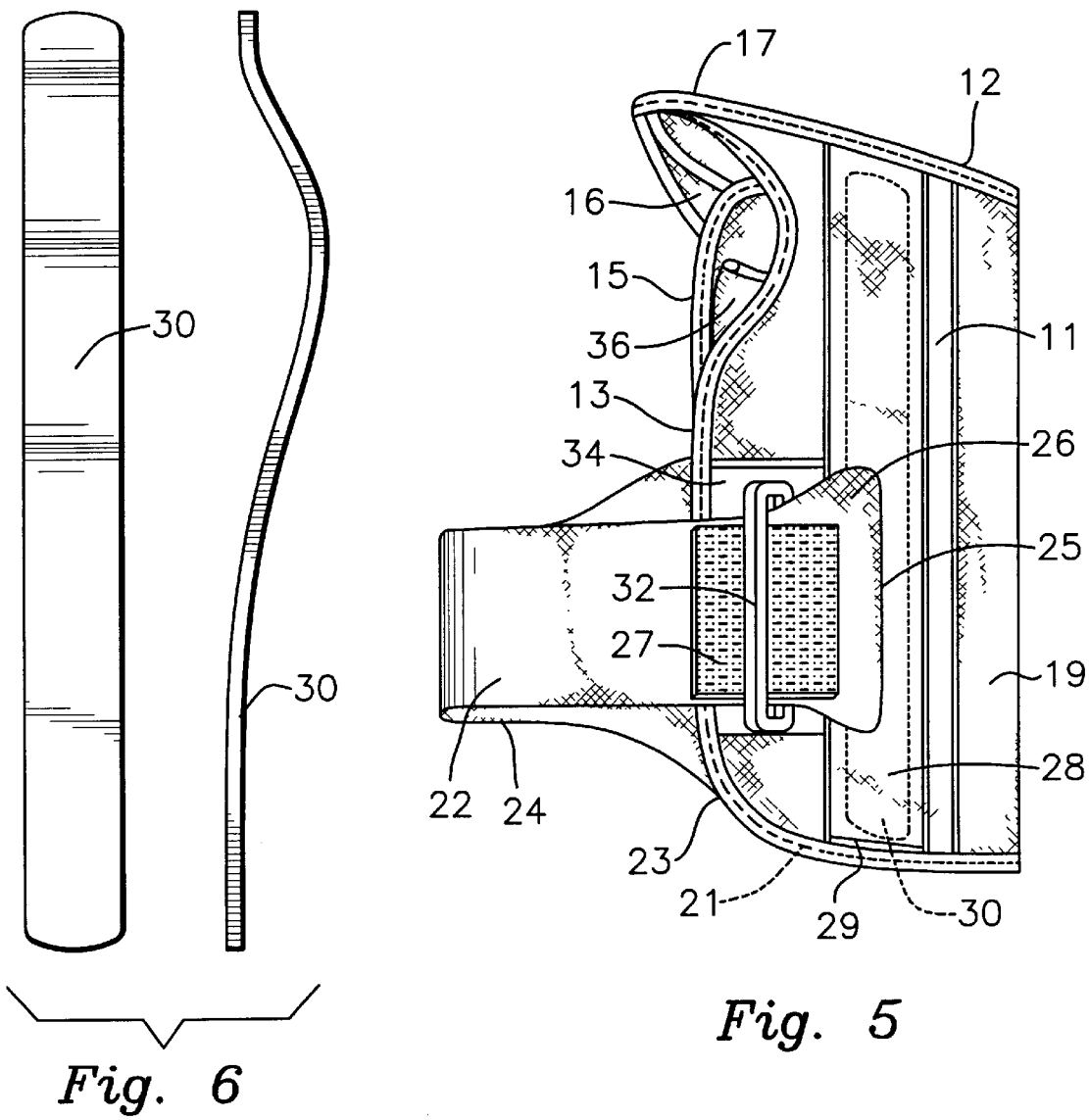
FIG. 5 is a bottom view of the wrist brace of the invention in position for use.
FIG. 6 is a composite view illustrating a front plan and side elevations of the stiffening insert also shown in dotted lines in FIG. 5 of the drawings.

Referring now to FIG. 6 of the drawings, a metal reinforcing brace 30 can be seen having a transversely flat main body member which is longitudinally curvilinear of a dimensional aspect so as to be registerable within the pocket P via the opening at 29 and to provide a contoured rigid support which will correspond to the anatomy of a human wrist R, best seen in FIGS. 1 and 4 of the drawings.

An elongated fabric loop 31 extends longitudinally along a portion of the pocket P in transverse alignment with the hereinbefore described strap 22. A D-ring 32 extends through and from the loop 31 and provides for engageable registration of the strap 22 as will be described in greater detail hereinafter.

A first strap fixation area 33 formed of velcro type loop material extends between the upper and lower edges 12 and 14 adjacent the opposite side edge 15 and is secured to the main pad 11 by sewing. An elongated pocket 33 A is defined within the fixation area 33 to receive a semi-rigid insert brace element 33B shown in dotted lines. A second strap fixation area 34 formed again of velcro loop material is secured to the pad 11 at right angles from the first strap fixation area 33 in transverse alignment to the strap 22. A third area 35A of velcro type hook material is secured to the pad 11 angularly from the upper portion of the fixation area 33. A pad 35 of loop material is secured to the pad 11 along its side edge 13 to the pocket adjacent the fabric loop 31 attachment point, again as best illustrated in FIG. 1 of the drawings to provide a padded surface for engagement of the D-ring 32.

Figure 2:
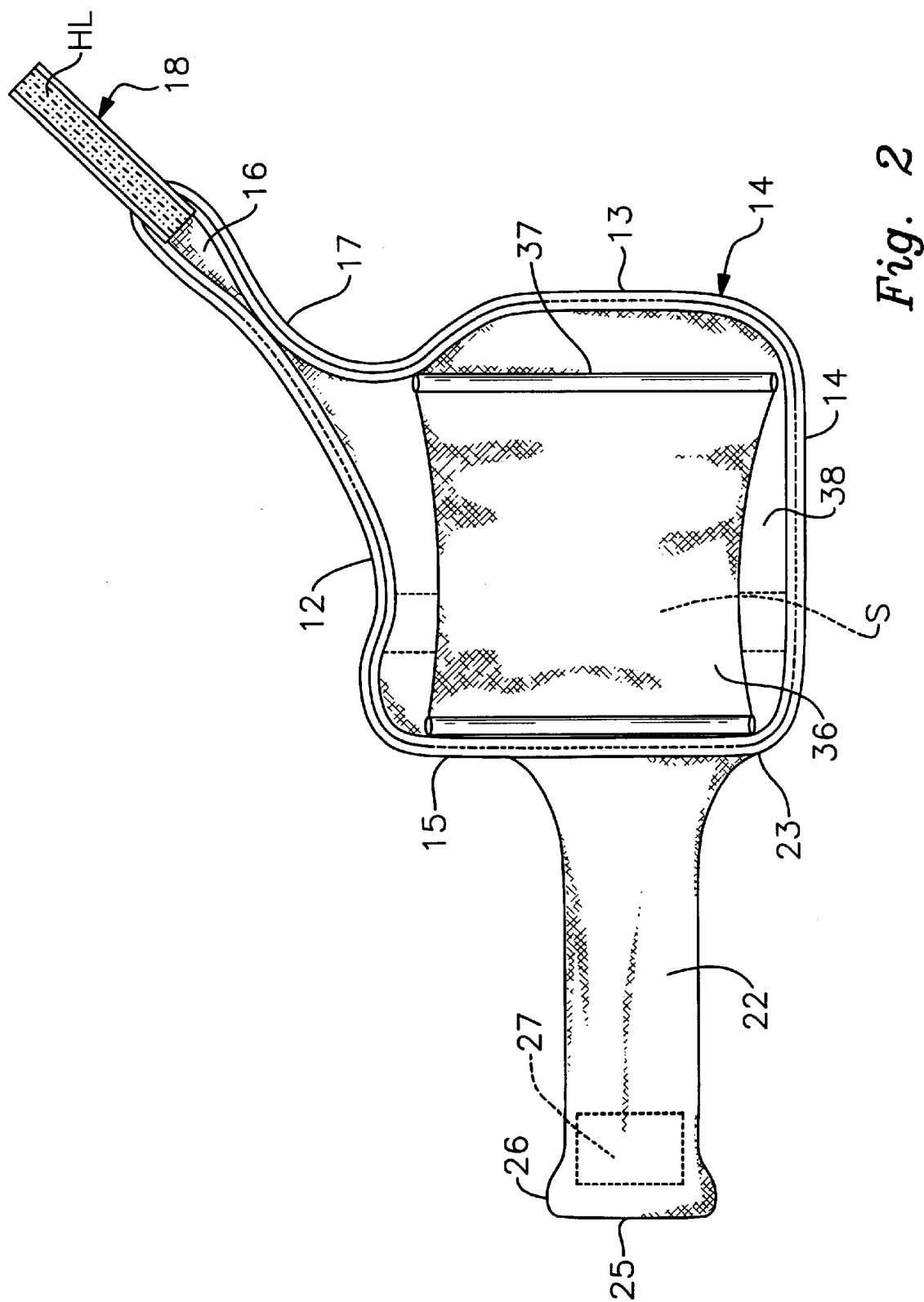
FIG. 2 is a bottom plan view of the wrist brace of the present invention.

Referring now to FIG. 2 of the drawings, the inside surface 38 of the wrist brace 10 of the invention can be seen having an elastic band 36 extending from the inside edge 15 adjacent the strap 22 to an attachment point 37 inwardly of the oppositely disposed edge portion 13. The elastic band 36 defines a sleeve between itself and the inside surface 38 of the pad 11.

Figure 3:
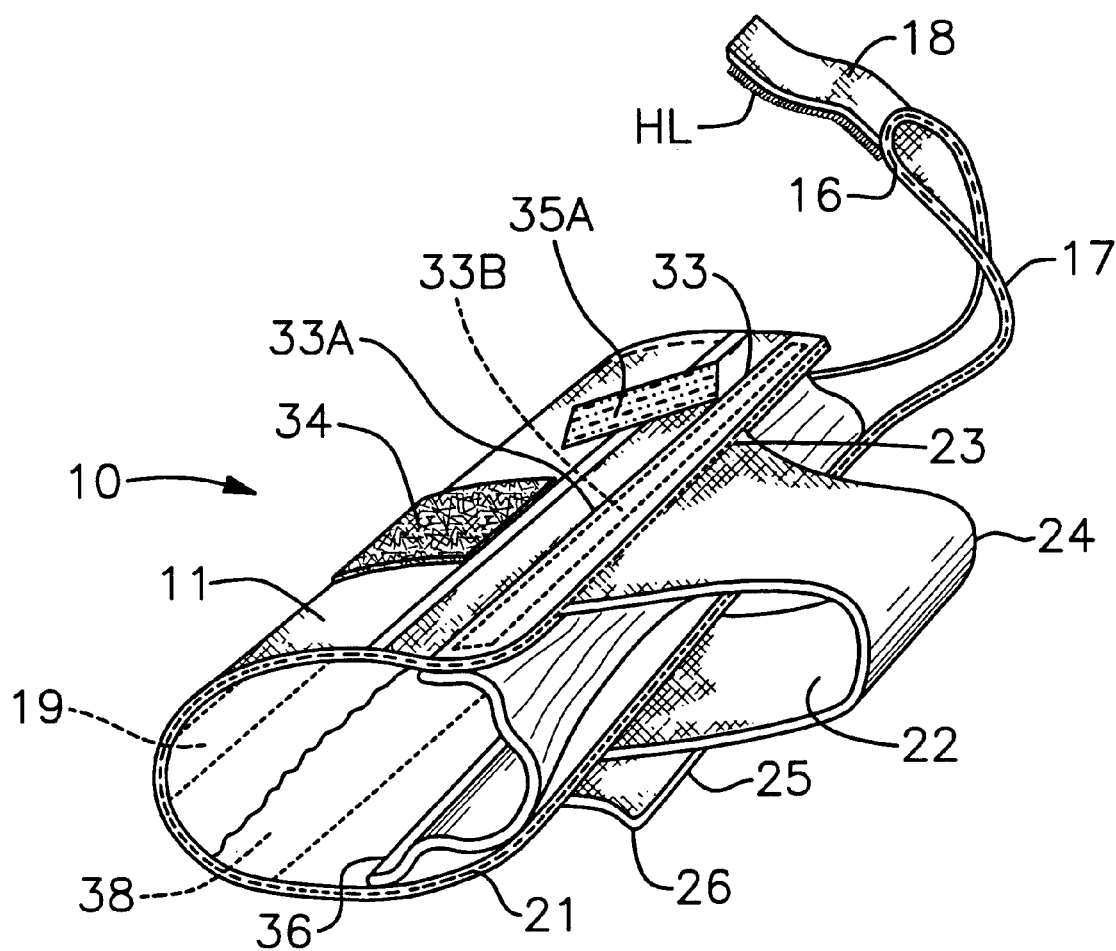
FIG. 3 is a perspective view of the wrist brace of the invention in use position for insertion of the user's wrist and hand.

Referring now to FIGS. 3 and 5 of the drawings, the wrist brace 10 of the invention can be seen in its "as used" position wherein the strap 22 is inserted through the D-ring 32 and the pad 11 folded generally along the reinforcing strip 19. The thumb strap 16 extends over for engagement on the first strap fixation area 35A via the fixation strap 18 extending therefrom as hereinbefore described.

The sleeve S formed between the inside surface 38 of the pad 11 and the elastic band 36 will allow for one-handed application by the user who may be disabled or otherwise infirmed.

Referring to FIG. 4 of the drawings, the wrist brace 10 can be seen on the user's wrist R and hand H with the elastic band 36 expanded about the user's wrist R. The thumb strap 16 has been adjustably secured about the hand H between the thumb T and index finger F of the hand H as will be apparent to those skilled in the art. Correspondingly, the strap 22 has been pulled tight on itself through the D-ring 32 and selectively secured to the pad 11 at the first strap fixation area 33 by engagement of the velcro type pad 27 thereon. The combination of the elastic strap 22, the single D-ring 32 that is self-adjusting, easy to use and eliminates need for additional strapping and the hereinbefore described elastic band 36 impart a secure, but yet comfortable fit of the wrist band about the user's wrist R.

It will be noted that the reinforcing bar 30 shown in FIG. 6 of the drawings is inserted within the pocket P on the pad 11's outer surface as seen in FIGS. 1 and 3 of the drawings provides a contoured rigid support to the wrist R and engagement portion of the hand H within the structure of the wrist brace 10.

Referring back now to FIGS. 1 and 5 of the drawings, it will also be evident that the elastic strap 22 area of attachment to the opposite edge 15 of the pad 11 defining the attachment area 23 as hereinbefore disclosed encompasses a greater area of the opposite edge 15 of the pad then that of the attachment point of the fabric loop 31 and associated D-ring 32 so as described in use when the strap 22 is threaded through the D-ring 32 and then reversed upon itself and pulled backwardly across the elastic band 36 and secured adjacent the point of attachment 23, it will be evident that a uniform elongated supporting tensional surface is derived at the point of attachment 23 greater than that of the engagement area defined in the D-ring 32 and loop 31 imparting a uniform securing arrangement for the pad 11's portion defined by the edge 15 and thus securing the pad securely and uniformly and evenly about the wrist R of the user as illustrated in FIG. 4 of the drawings imparting a superior closure to the configuration.

It will be apparent to those skilled in the art that various changes and modifications may be made therein without departing from the spirit of the invention.

Therefore I claim:

1. A wrist brace to be positioned about the wrist and dorsal area of the hand to apply support to the wrist and hand for therapeutic purposes, the wrist brace comprises an elongated pad of synthetic non-resilient material composition have adjacent contoured edge portions and adjacent long edge portions, a thumb strap extending angularly from said respective contoured edge portions, a securing strap extending from one of said adjacent long edge portions on said elongated pad, a buckle means extending from one side of said pad inwardly from one of said contoured edge portions in oppositely disposed relation to said securing strap, said securing strap extending from an elongated point of attachment to one of said long edge portions, said point of attachment being of a width greater than that of of said securing strap, a resilient band extending from an inner surface of said elongated pad adjacent an opposing long edge to a point inwardly of one of said contoured edges defining a sleeve therebetween, means for selectively securing said thumb strap and said securing strap to and outer surface of said elongated pad and rigid reinforcing members within elongated pockets in and outer surface of said pad.

2. The Wrist brace set forth in claim 1 wherein said means for securing said securing strap to the outer surface of said elongated pad comprises a first attachment strip of hook and loop material secured to said outer surface of said elongated pad along its long edge adjacent said elongated point of attachment for said securing strap, a second attachment strip of hook and loop material secured to said outer surface extending from said first attachment strap at right angles thereto, said securing strap having registerable hook and loop material thereon for selective registration with said first and second attachment strips.

3. The wrist brace set forth in claim 2 wherein said means for securing said thumb strap to the outer surface of said elongated pad comprises a third area of hook and loop material extending angularly from said first area of hook and loop material.

4. The wrist brace set forth in claim 1 wherein said securing strap is of an elastic material and is engageable through said buckle means for return upon itself for selective attachment to said elongated pad.

5. The wrist brace set forth in claim 1 wherein said buckle means comprises a D-ring extending from a fabric loop secured to said outer surface of said elongated pad.

6. The wrist brace set forth in claim 1 wherein one of said reinforcing members registerable within one of said elongated pockets on the outer surface of said elongated pad comprises an elongated transversely flat contoured ridge metal bar.

7. The wrist brace set forth in claim 1 wherein said securing strap has a transverse tab extensions adjacent its distal end.

8. The wrist brace set forth in claim 1 wherein said securing strap is of an elastic material having a known rebound property.

9. The wrist brace set forth in claim 1 wherein said elongated pad is formed of a synthetic laminate material having a resilient foam core and oppositely disposed non-elastic surface sheets bound together about its perimeter edge.

10. The wrist brace set forth in claim 1 wherein said reinforcing members registerable within said elongated pockets on the outer surface of said elongated pad comprises an elongated transversely flat semi-rigid bars.

\* \* \* \* \*